(12) United States Patent
Guennouni et al.

(10) Patent No.: US 7,659,417 B2
(45) Date of Patent: Feb. 9, 2010

(54) PROCESS FOR OBTAINING HALOGENATED MONOORGANOXYSILANES WHICH CAN BE USED IN PARTICULAR AS SYNTHESIS INTERMEDIATES

(75) Inventors: Nathalie Guennouni, Irigny (FR); Gérard Mignani, Lyons (FR); Virginie Pevere, Lyons (FR)

(73) Assignee: Rhodia Operations, Aubervilliers (FR)

( * ) Notice: Subject to any disclaimer, the term of this patent is extended or adjusted under 35 U.S.C. 154(b) by 0 days.

(21) Appl. No.: 12/320,567

(22) Filed: Jan. 29, 2009

(65) Prior Publication Data

US 2009/0177003 A1    Jul. 9, 2009

Related U.S. Application Data

(63) Continuation of application No. 10/489,836, filed as application No. PCT/FR02/03067 on Sep. 10, 2002.

(30) Foreign Application Priority Data

Sep. 21, 2001  (FR) .................................. 01 12191
Dec. 20, 2001  (FR) .................................. 01 16508

(51) Int. Cl.
    *C07F 7/18* (2006.01)
(52) U.S. Cl. .................... 556/427; 556/463; 556/482
(58) Field of Classification Search ................ 556/427, 556/463, 482
    See application file for complete search history.

(56) References Cited

U.S. PATENT DOCUMENTS

| 4,125,552 A | 11/1978 | Speier |
| 4,401,826 A | 8/1983 | Selin |
| 4,507,490 A | 3/1985 | Panster et al. |
| 5,107,009 A | 4/1992 | Rauleder et al. |
| 5,117,027 A | 5/1992 | Bernhardt et al. |
| 5,650,457 A | 7/1997 | Scholl et al. |
| 6,242,627 B1 | 6/2001 | Gedon et al. |
| 6,774,255 B1 | 8/2004 | Tardivat et al. |
| 2004/0051210 A1 | 3/2004 | Tardivat et al. |

FOREIGN PATENT DOCUMENTS

| DE | 26 48 241 | 6/1977 |
| DE | 27 49 316 B1 | 8/1978 |
| EP | 0 471 164 A1 | 4/1992 |
| EP | 0 680 997 A1 | 11/1995 |
| WO | WO 98/52954 | 11/1998 |
| WO | WO 0230939 A1 | 4/2002 |
| WO | WO0231041 A1 | 4/2002 |

OTHER PUBLICATIONS

International Search Report for PCT/FR02/03067 dated Jan. 23, 2003.

*Primary Examiner*—Elvis O Price
(74) *Attorney, Agent, or Firm*—Buchanan, Ingersoll & Rooney P.C.

(57) ABSTRACT

The invention concerns the preparation of halogenated monoorganoxysilanes, of formula (I),

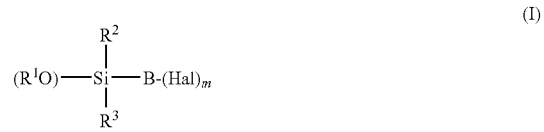

said compounds being useful as synthesis intermediate in organic chemistry. Said method for preparing monoorganoxysilanes consists in: using as starting product halogenoalkylsilanes of the $(CH_3)_2SiCl_2$ type and in substituting the silicon with a radical bearing a divalent unit bound to an electrophilic reactive group capable of reacting with at least an appropriate nucleophilic agent to form a functionalised monoorganoxysilane of formula (II)

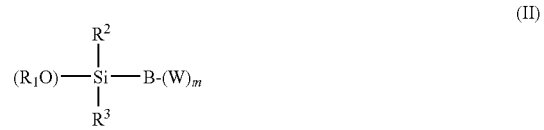

9 Claims, No Drawings

PROCESS FOR OBTAINING HALOGENATED MONOORGANOXYSILANES WHICH CAN BE USED IN PARTICULAR AS SYNTHESIS INTERMEDIATES

CROSS-REFERENCE TO PRIORITY/PCT APPLICATIONS

This application is a continuation of U.S. patent application Ser. No. 10/489,836, filed Aug. 30, 2004 as the National stage of International Application Number PCT/FR02/03067 filed on Sep. 10, 2002, each hereby expressly incorporated by reference and each assigned to the assignee hereof. PCT/FR02/03067 claims priority to French Application 01/16508, filed Dec. 20, 2001, and to French Application 01/12191, filed Sep. 21, 2001.

The present invention relates to novel pathways for synthesizing halogenated monoorganoxy-silanes, and also to the use of these monoorganoxy-silanes as synthesis intermediates in organic chemistry, for producing monoorganoxysilanes functionalized with groups other than a halogen. The invention is also directed towards the compositions containing such synthesis intermediates in organic chemistry.

The synthesis intermediates in organic chemistry to which reference is made in the context of the invention are particularly useful in the preparation of monoorganoxysilanes functionalized, for example, with amino, thiol or polysulfide groups.

One of the essential aims of the present invention is to provide an improvement to the synthesis of halogenated monoorganoxysilanes, in particular useful as synthesis intermediates in organic chemistry.

Another essential aim of the invention is to provide a process for preparing halogenated monoorganoxysilanes which is simple, industrial and relatively inexpensive.

Another essential aim of the invention is to provide a process for preparing halogenated monoorganoxysilanes capable of reacting with a nucleophilic agent to produce monoorganoxysilanes functionalized, for example, with amino, thiol or polysulfide groups.

Another essential aim of the invention is to provide a process for preparing halogenated monoorganoxysilanes, which provides a high yield, high selectivity and good productivity.

Another essential aim of the invention is to provide a process for preparing halogenated monoorganoxysilanes, in which the consumable reagents are commercial products available on a large scale.

Another essential aim of the invention is to provide novel intermediates for synthesis of monoorganoxysilanes functionalized, for example, with amino, thiol or polysulfide groups.

These aims, among others, are achieved by the present invention, which relates, firstly, to a process for preparing halogenated monoorganoxysilanes of formula:

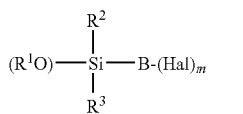
(I)

in which:
the symbol $R^1$ represents hydrogen, or a monovalent hydrocarbonaceous group chosen from a linear or branched alkyl radical having from 1 to 4 carbon atoms and a linear or branched alkoxyalkyl radical having from 2 to 8 carbon atoms;

the symbols $R^2$ and $R^3$, which may be identical or different, each represent a group a linear or branched alkyl radical having from 1 to 6 carbon atoms, an aryl radical having from 6 to 18 carbon atoms, an arylalkyl radical or an alkylaryl radical ($C_6$-$C_{18}$ aryl; $C_1$-$C_6$ alkyl);

m=1 or 2;

the symbol Hal represents a halogen atom chosen from chlorine, bromine and iodine atoms;

B:
when m=1: divalent residue of formula:

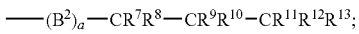

with:
the condition according to which one of the radicals $R^7$, $R^8$, $R^9$, $R^{10}$, $R^{11}$, $R^{12}$, $R^{13}$ corresponds to a valency bond;

$B^1$=linear or branched $C_1$-$C_{10}$ alkylene residue; divalent aromatic residue chosen from:
- -(ortho-, meta- or para-)phenylene-(linear or branched $C_2$-$C_6$)alkylene-,
- -(linear or branched $C_2$-$C_6$)alkylene-(ortho-, meta- or para-)phenylene-, and
- -(linear or branched $C_2$-$C_6$)alkylene-(ortho-, meta- or para-)phenylene-(linear or branched $C_2$-$C_6$)alkylene- $B^2$=linear or branched $C_1$-$C_{10}$ alkylene residue; divalent aromatic residue chosen from:
- -(ortho-, meta- or para-)phenylene-(linear or branched $C_2$-$C_6$)alkylene-,
- -(linear or branched $C_2$-$C_6$)alkylene-(ortho-, meta- or para-)phenylene-, and
- -(linear or branched $C_2$-$C_6$)alkylene-(ortho-, meta- or para-)phenylene-(linear or branched $C_2$-$C_6$)alkylenea=0 or 1;

$R^4$ to $R^{13}$, which may be identical or different, each represent hydrogen, or a group a linear or branched alkyl radical having from 1 to 3 carbon atoms, when m=2: trivalent residue of formula:

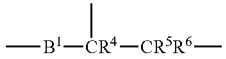

with $B^1$, $R^4$, $R^5$, $R^6$ as defined above;
characterized in that it comprises the following steps -a-, -b- and -c-

Step -a-

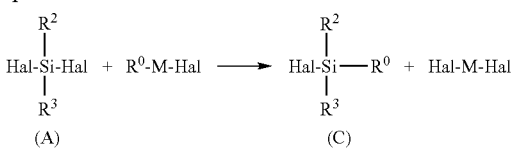

with
$R^0$ representing independently:
$R^{01}$ corresponding to: $CR^5R^6$=$CR^4$—$B^1$—;
$R^{02}$ corresponding to:
$CR^{11}R^{12}R^{13}$—$CR^9R^{10}$—$CR^7R^8$—$(B^2)_a$—; with at least one of the radicals $R^7$ to $R^{13}$ representing hydrogen;

the symbol M representing an alkali metal or an alkaline earth metal;

Step -b- when $R^0=R^{01}$:

either:

(C) + H-Hal ⟶

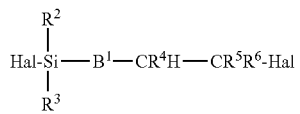

and/or

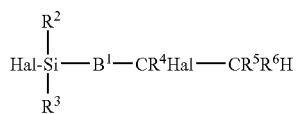

it being possible for the products thus obtained, when they are in a mixture, to be introduced in step -c-, either as a mixture, or separately after separation;

or:

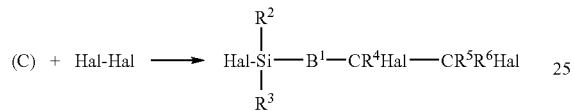

when $R^0=R^{02}$

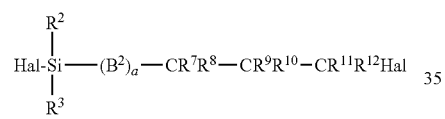

and/or

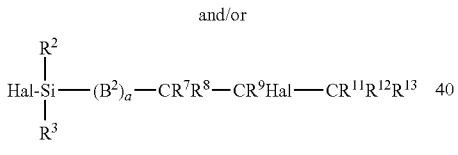

and/or

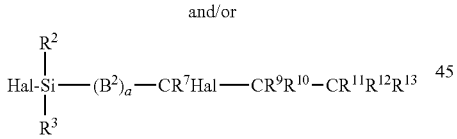

(in the case where $R^{13}$ and/or $R^{10}$ and/or $R^8=H$) it being possible for the products thus obtained, when they are in a mixture, to be introduced in step -c-, either as a mixture, or separately after separation;

Step -c-

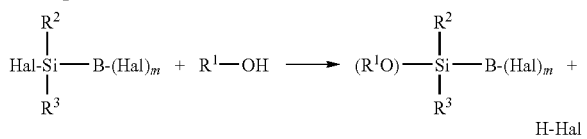

In accordance with the invention, the symbol Hal preferably denotes chlorine.

The process according to the invention makes it possible to obtain halogenated monoorganoxysilanes in a simple and industrial manner starting from haloorganosilanes (for example $Me_2SiCl_2$ where $Me=CH_3$), which are major intermediates of direct synthesis (Rochow-Muller synthesis from Si and from MeCl). These are the raw materials for the industrial production of silicones. The main advantages of the process according to the invention are in terms of the cost and of the industrial accessibility of the products used, and in particular of the starting products.

In formula (I) above, the preferred radicals $R^1$ are chosen from the radicals: methyl, ethyl, n-propyl, isopropyl, n-butyl, $CH_3OCH_2$—, $CH_3OCH_2CH_2$— and $CH_3OCH(CH_3)CH_2$—; more preferably, the radicals R1 are chosen from the radicals: methyl, ethyl, n-propyl and isopropyl.

The preferred radicals $R^2$ and $R^3$ are chosen from the radicals: methyl, ethyl, n-propyl, isopropyl, n-butyl, n-hexyl and phenyl; more preferably, the radicals $R^2$ and $R^3$ are methyls.

Preferably, in the halogenated monoorganoxysilanes corresponding to formula (I), the radical B may represent an alkylene which corresponds to the formulae below:

—$(CH_2)$—, —$(CH_2)_2$—, —$(CH_2)_3$—,

—$(CH_2)_4$—, —$(CH_2)$—$CH(CH_3)$—,

—$(CH_2)_2$—$CH(CH_3)$—,

—$(CH_2)_2$—$CH(CH_3)$—$CH_2$—,

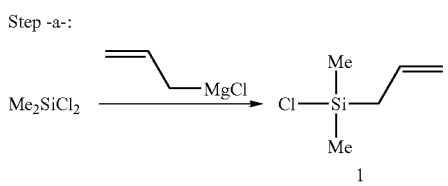

—$CH_2$—$CH(CH_3)$—$CH_2$—;

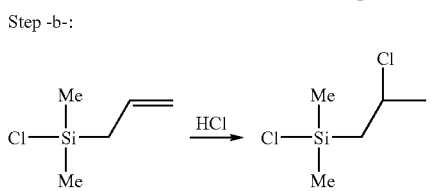

In summary and by way of example, the variant $R^0=R^{01}$ can be illustrated as follows:

Step -a-:

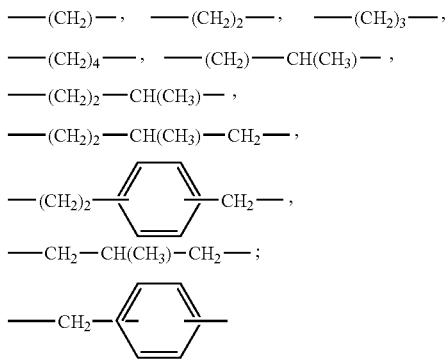

Step -b-:

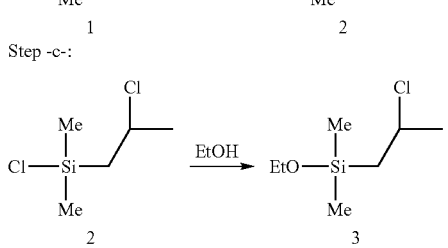

Step -c-:

In the preceding example, the process according to the invention here consists in reacting an allylmagnesium chloride on $Me_2SiCl_2$. The procedure therefore consists in reacting chloroalkylsilanes with a suitable Grignard reagent, in accordance with the procedures described in the two publications below:

K. ANDRIANOV et al., Zhur Obsh. Khim, 8 (1938) 969

M. VORONKOV et al., idem 25 (1955) 1142

These syntheses are carried out in two steps:
1) Preparation of the allyl or methallyl Grignard according to conventional processes (see the procedures described in: "Grignard Reactions of Nonmetallic Substances, Kharasch & Reinmuth, Prentice-Hallu, Inc, 1954"),
2) Addition of the Grignard to the chloromethylsilanes in an ether-type solvent.

The following derivatives are already described in the literature:

⇒ClMe$_2$Si—CH$_2$—CH=CH$_2$: D. HURD et al., J. Am. Chem. Soc., 67 (1945) 1813, ⇒ClMe$_2$Si—CH$_2$—CMe=CH$_2$: H. HURD et al., Ind. Eng. Chem. 40 (1948) 2078.

It is also possible to perform this synthesis in a single step by mixing, for example, the magnesium, the allyl chloride and the chloromethylsilane at a temperature in the region of 5-20° C. (U.S. Pat. No. 5,629,439 of May 13, 1997, DOW CORNING).

Also by way of example, it may be indicated that the action of the Grignard reagent derived from crotyl chloride makes it possible to produce the following silane:

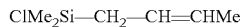
ClMe$_2$Si—CH$_2$—CH=CHMe

As regards step -b- in this variant $R^o=R^{01}$, the process consists in reacting H-Hal, e.g. HCl, with the unsaturated silane (C), e.g. the silane referred to as 1 in the example of the variant $R^o=R^{01}$ summarized above. The operating conditions are provided by the studies described in the following reference: V. D. Sheludyakov et al., Zh. Obsh. Khim. (1985) 1202.

Thus, in the context of a particularly preferred embodiment of the process according to the invention, the operating protocol consists in adding, for example, HCl gas to the allylsilane in the presence of a Lewis acid, e.g. of the FeCl$_3$ type (it is also possible to use other Lewis acids such as: AlCl$_3$, ZnCl$_2$ or mixtures thereof). The catalyst/silane molar ratio ranges between 0.01 and 0.1, at a temperature of between 30 and 70° C. The silane is obtained with a yield at least equal to 85%. The solvent used for this reaction may be toluene (or xylene or chlorobenzene or dichlorobenzene, pure or as a mixture,— an a polar aprotic solvent is required—it is also possible to use, for example, CCl$_4$, dichloroethane). It is possible to work in bulk. The rate of introduction of the HCl is of the order of 3-6 liters/h. The derivative is isolated by distillation under reduced pressure. The by-products of this reaction consist mainly of a derivative (D), which results from the reverse addition of HCl, and the formula of which is given below.

(D)

This derivative is a precursor of the halogenated monoalkoxysilane (I) which is the aim.

It is possible to obtain (D) directly by the action of HCl with the silane (C) under UV initiation. It is possible to modify the direction of the addition of HCl to an unsaturation according to the operating conditions. According to thermal processes, the addition takes place according to the Markovnikov rule, i.e. the chlorine atom will preferentially go to the carbon richest in electrons. If the reaction is carried out under UV, this rule is not observed, and the reverse addition mainly occurs.

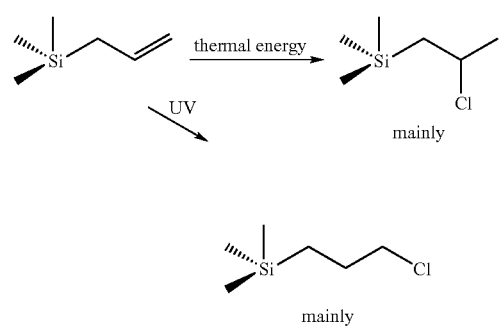

For more details, it is recommended to refer to the work: "March's Advanced Organic Chemistry". M. B. SMITH and J. MARCH. Fifth Edition. John Wiley & Sons, Inc. 2001, page 985 and cited references.

Similarly, it is possible to add HBr and HI. From an industrial point of view, it is advantageous to use HCl.

The addition of HCl, for example under thermal conditions, to a methyallylsilane derivative results in the silane (D):

ClMe$_2$Si—CH$_2$—CMe$_2$Cl

In the variant $R^o=R^{02}$, the halogenation of the chain $R^o$ with the Hal group is carried out using (Hal$_2$ and/or SO$_2$(Hal)$_2$ (step -b-).

In summary and by way of example, this variant $R^o=R^{02}$ can be illustrated as follows:

Step -a-:

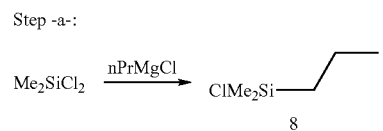

Step -b-:

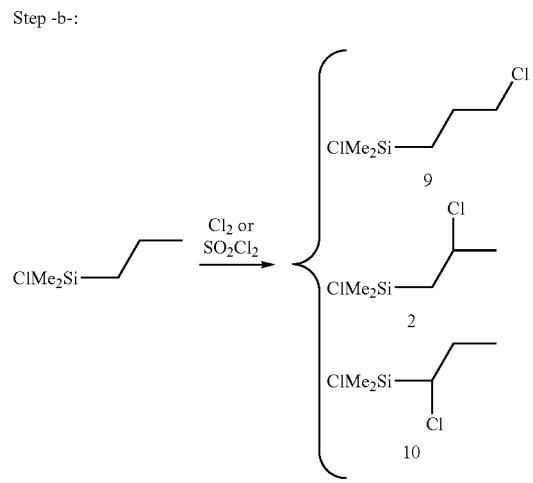

Step -c-:

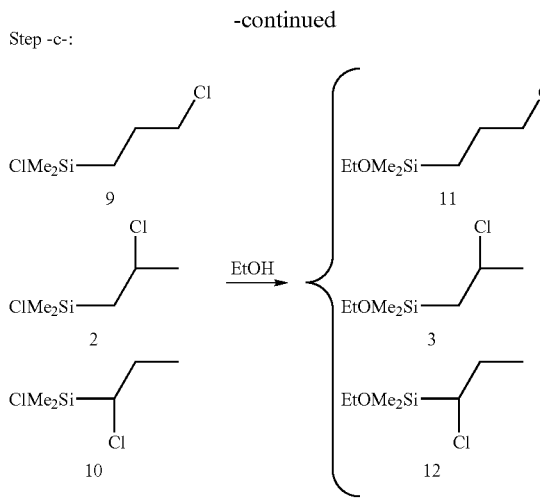

Step -a- consists, in practice, in reacting e.g. an organolithium reagent or a Grignard reagent with $Me_2SiCl_2$ in a polar aprotic solvent.

The chlorination step -b- is described in the literature. For example: L. SOMMER et al., J. Am. Chem. Soc., 68 (1946) 488 and V. MIRONOV et al., Izv. Adakd. Nauk. SSSR., Otdel. Khim. Nauk., (1955) 182. A mixture of these three compounds is generally obtained in a ratio which depends on the nature of the chlorinating agent. For $SO_2Cl_2$, the following ratios are observed: ~5~45~50 between 10/2/9. The use of chlorine makes it possible to very greatly reduce the amount of derivative 10. The isolated yields are of the order of 75-80%.

In practice, in these variants $R^\circ=R^{01}$ and $R^\circ=R^{02}$, the alkoxylation (step -c-), advantageously the ethoxylation, occurs after the substitution with the hydride of Hal (step -b-). It is carried out using at least one alcohol $R^1OH$ (with $R^1=C_1$-$C_4$, preferably $C_2$, alkyl). In practice, this alkoxylation is carried out in a manner known to those skilled in the art, according to a process of alcoholysis as described, for example, in patent DE 19 734 295 or U.S. Pat. No. 5,892,085.

It is not a departure from the present invention to carry out the following operations (1), (2) and (3):

operation (1) where, in performing steps -a-, -b- and -c-, the two steps -a- and -b- where m=1 are replaced with the single step -a'- or -a"- below:

-Step-a'-

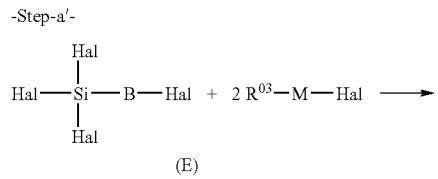

-Step-a"-

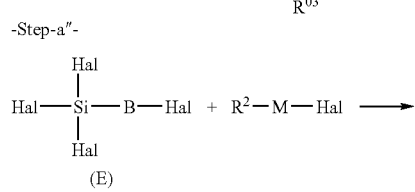

-continued

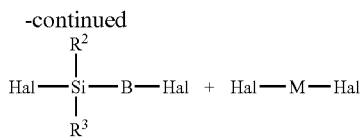

where the symbols Hal, B and M are as defined above, the symbol $R^{03}$ corresponds to $R^2$ and/or $R^3$ also as defined above, and the compound of formula (E) is prepared by reacting, for example, the trihalosilane $(Hal)_3SiH$ with the unsaturated precursor compound of the group B—Hal, in particular the compound $CR^5R^6=CR^4-B^1$—Hal with $R^5$, $R^6$ and $B^1$ having the definitions also given above;

operation (2) where, in carrying out the process, the three steps -a-, -b-, and -c- where m=1 are replaced with the three steps -a1-, -b1- and -c1- below:

-Step -a1-

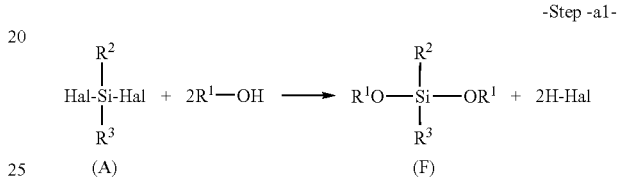

where the symbols Hal, $R^2$, $R^3$ and $R^1$ are as defined above,

-Step -b1-

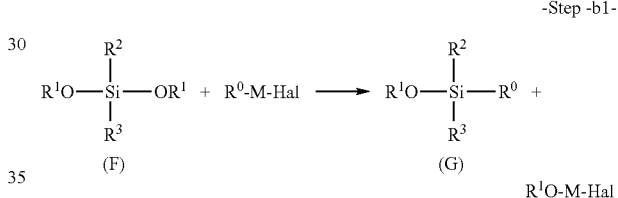

where the symbols $R^1$, $R^2$, $R^3$, $R^0=R^{01}$ or $R^{02}$, M and Hal are as defined above, Step -c1-, during which either the group $R0=R^{01}$ of formula (G) is hydrohalogenated, or the group $R^0=R^{02}$ of formula (G) is halogenated, so as to produce the group B—Hal, this being carried out using either the reagent H-Hal or the reagents Hal-Hal and/or $SO_2(Hal)_2$ as indicated above in step -b-;

operation (3) where, in carrying out steps -a1-, -b1- and -c1-, these three steps where m=1 are replaced with the single step -a'''- below:

- step -a'''-

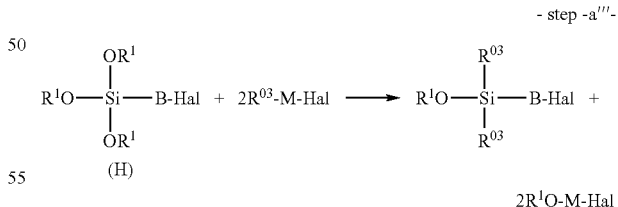

where the symbols $R^1$, B, Hal, $R^{03}$ and M are as defined above, and the compound of formula (H) is prepared, for example, (i) by reacting the trihalosilane $(Hal)_3SiH$ with the unsaturated precursor compound of the group B—Hal, in particular the compound $CR^5R^6=CR^4-B^1$—Hal as defined above, so as to form the compound $(Hal)_3Si-B-Hal$ (J), and then (ii) by alkoxylating the compound of formula (J) according to a conventional process of alcoholysis using the alcohol $R^1$—OH so as to form the compound of formula (H).

Steps -b1- and -a'''- can be carried out under conditions, for example, similar to those described in Japanese patent 2,178, 293.

In accordance with the invention, the product (I):

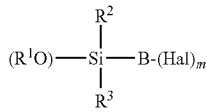
(I)

obtained at the end of step -c- or -c1- or -a'''- is a synthesis intermediate capable of reacting with at least one nucleophilic agent for the production of functionalized organosilanes of formula (II):

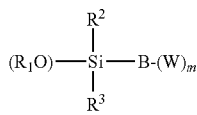
(II)

in which $R^1$, $R^2$, $R^3$, B and m are as defined above, and W is an organic monovalent functional group, preferably chosen from the set comprising the radicals: alkoxyl, acyl, amino, which may or may not be substituted, mercapto, cyano, thiocyanato, oxycyanato and (organosilyl)organopolythio, and mixtures thereof.

The nucleophilic agent may be an alkoxide. In this case, when m=1, the reaction scheme is as follows:

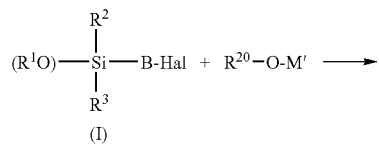
(I)

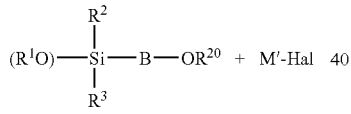

with M' chosen from the alkali metals, and with $R^{20}$ corresponding to the same definition as that given above for $R^1$.

The nucleophilic agent may be a carboxylic acid salt. In this case, when m=1, the reaction scheme is as follows:

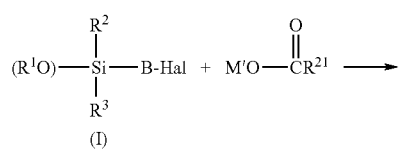
(I)

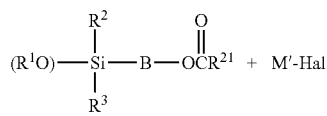

with M' chosen from the alkali metals, with $R^{21}$ corresponding to the same definition as that given above for $R^1$ and possibly also corresponding to $C_2$-$C_{10}$ alkenyl, optionally substituted with $C_1$-$C_3$ alkyl.

Preferably, the acid considered is (meth)acrylic acid. In other words:

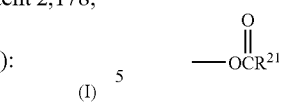

corresponds to a meth(acrylate) radical.

The nucleophilic agent may be an amine. In this case, when m=1, the reaction scheme is as follows:

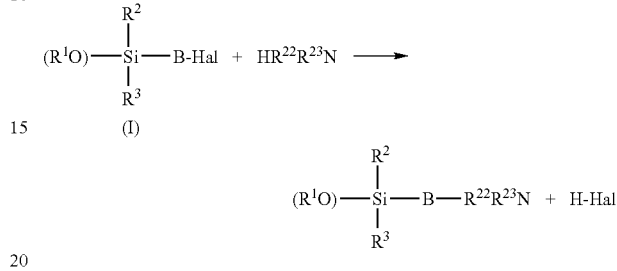

with $R^{22}$ and $R^{23}$ corresponding to the same definition as that given above for $R^1$.

With regard to this reaction, it may be specified that this amine function-containing compound can be obtained by reaction of the halosilane in the presence of anhydrous ammonia in the particular case where $R^{22}$=$R^{23}$=H, under pressure, for example under conditions similar to those described in the Dynamit Nobel patent DE-2 749 316 from 1977, namely: autogenous pressure in the presence of $NH_3$ (30 equivalents) and reaction carried out for 12 hours at 100° C.

The nucleophilic agent may be a sulfur-containing derivative making it possible to obtain an organosilane of formula (II) bearing a mercapto (or thiol) function. In this case, when m=1, the reaction scheme is as follows:

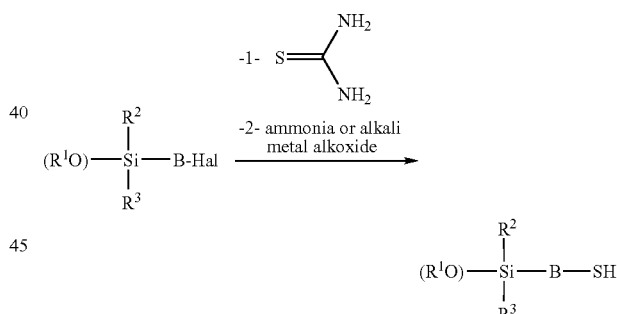

With regards to this reaction, it may be specified that the thiol function-containing compound of formula (II) can be obtained in two steps, namely:

Step 1=reaction in the presence of bulk thiourea at ambient temperature,

Step 2=reaction of the intermediate obtained in step 1 with $NH_3$ gas under autogenous pressure at 100° C. or reaction with an alkali metal alkoxide.

The nucleophilic agent may be a nitrile. In this case, when m=1, the reaction scheme is as follows:

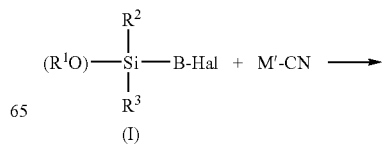
(I)

-continued

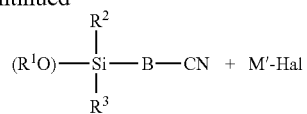

with M' chosen from the alkali metals.

With regard to this reaction, it may be specified that this cyano function-containing compound can be obtained by reaction of the halosilane with an alkali cyanide; for example under conditions similar to those described in Union Carbide U.S. Pat. No. 3,177,236 (1965), namely: anhydrous NaCN in dimethylformamide, 6 hours at 150° C.

The compound of formula (II) obtained can itself be reduced under known conditions, to give:

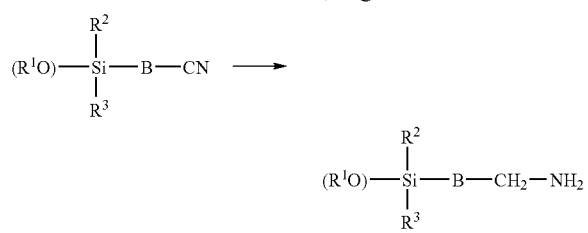

The nucleophilic agent may be a thio or an oxynitrile. In this case, the reaction scheme is as follows:

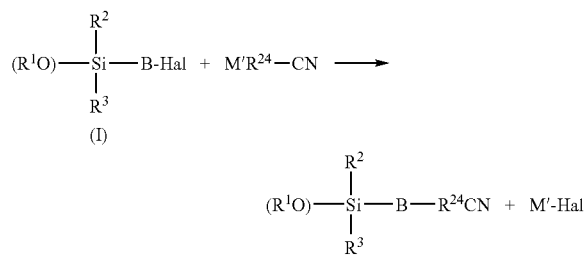

with M' chosen from the alkali metals and $R^{24}$=O or S.

The nucleophilic agent may be $M'_2S_x$. In this case, when m=1, the reaction scheme is as follows:

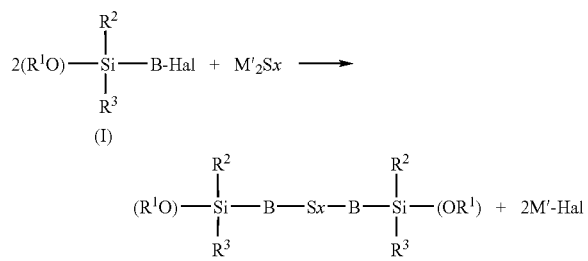

with M'=alkali metals,
x=integer or fraction ranging from 1.5 to 10, and preferably 2 to 5.

When W is a radical of the (organoxysilyl)-organopolythio type, the reaction in question is a sulfidation. This consists in reacting the halogenated monoorganoxysilane (I) obtained by the process according to the invention, with an anhydrous metal polysulfide of formula $M'_2S_x$, at a temperature ranging from −20° C. to 90° C., optionally in the presence of an inert polar (or nonpolar) organic solvent.

As regards the practical manner in which the abovementioned synthesis is carried out, reference will be made, for further details, to the content for example of EP-A-0 848 006, which illustrates, starting with other reagents, procedures applicable to carrying out the synthesis under consideration.

In accordance with the invention, the product (I) obtained at the end of step -c-, where m=2, is a synthesis intermediate capable of reacting in particular with the nucleophilic agent $M'_2Sx$. In this case, the reaction scheme is as follows:

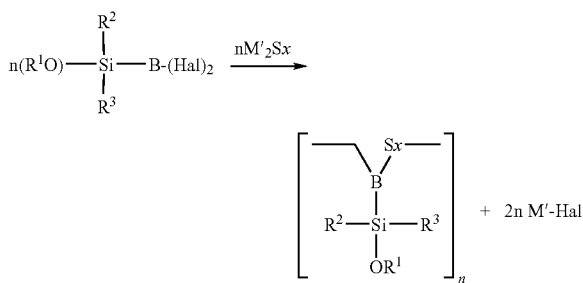

The processes according to the invention are applicable, for example, to the preparation of the halogenated monoorganoxysilanes of formulae:

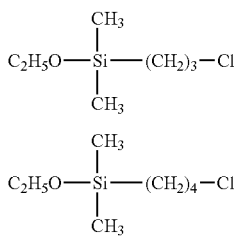

According to another of its subjects, the present invention concerns, by way of novel products, synthesis intermediate compositions comprising an effective amount of at least one alkoxysilane of formula:

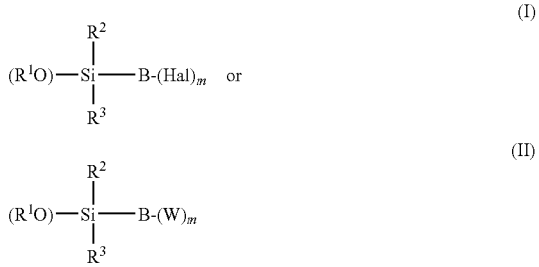

$R^1$, $R^2$, $R^3$, W, Hal, B and m being as defined above and possibly being obtained in particular by the process as presented above.

The following examples illustrate the present invention.

EXAMPLES

Example 1

The reaction scheme with which this example is concerned is as follows:

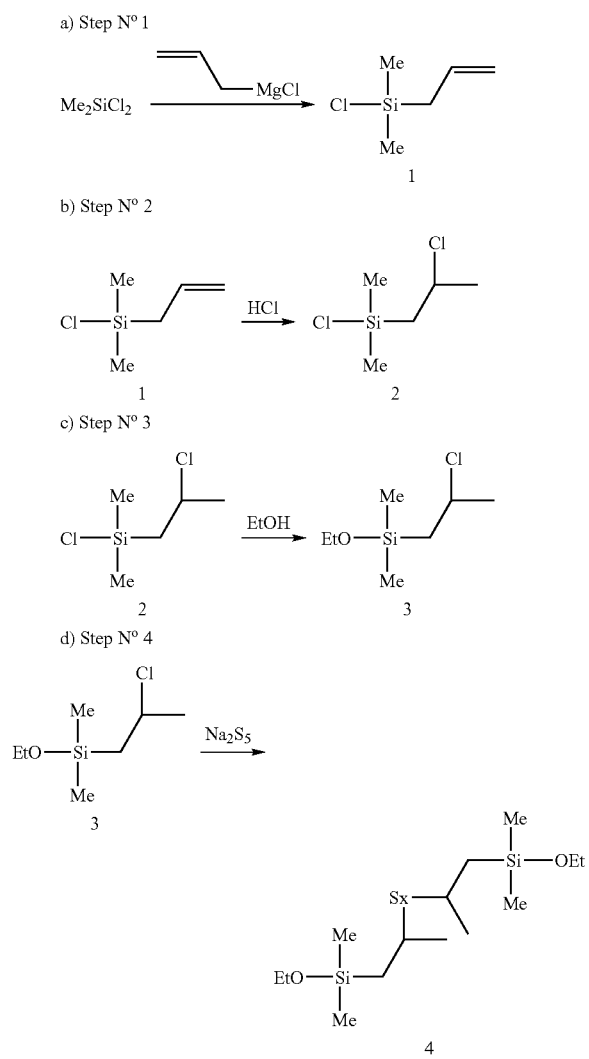

Step c) Ethoxylation:

513 g (3 mol) of the silane of structure 2 and 300 ml of toluene are introduced into a 2 liter reactor under nitrogen. 200 g of dry ethanol are added slowly. The temperature is kept around 50° C. During this operation the HCl is stripped with nitrogen. NaHCO$_3$ is subsequently added in order to neutralize the last remaining traces of HCl. Filtration is carried out and the solvent is then evaporated off. 541 g of the derivative 3 are recovered with a virtually quantitative yield.

Use of the Halogenated Alkoxysilane 3 as a Synthesis Intermediate in a Sulfidation Reaction:

91.9 g of sodium ethanolate (1.352 mol. i.e. the equivalent of 2 mol per mole of H$_2$S) in solution at 21 mass % in ethanol (438 g) and 250 ml of toluene are introduced, under a stream of argon, at the foot of a jacketed 1 liter reactor which is equipped with a refrigerant, a mechanical stirring device (Rushton turbine), a thermocouple, a gas (argon or H$_2$S) inlet pipe and an inlet for the peristaltic pump.

The mixture is stirred (200-300 rpm). A mass of 65 g of sulfur (2.031 mol, i.e. the equivalent of 3 mol per mole of H$_2$S) is then added.

After purging of the circuits with argon, the H$_2$S (23 g, i.e. 0.676 mol) is introduced by bubbling by means of an immersed tube, i.e. for 45-60 min. Heating at 60° C. is carried out for 1 h so as to complete the conversion to anhydrous Na$_2$S$_4$.

The mixture is allowed to cool to 25° C. A mass of 244 g (1.352 mol) of 3 is added by means of a peristaltic pump in 30 min (flow rate: 10 ml/min).

The reaction mass is heated at 75° C. for 4 h. It is then allowed to cool. Filtration is carried out. The cake is washed twice with dry toluene. Evaporation is carried out under a vacuum pump (3-4×10$^2$ Pa) at 70° C. 275 g of the derivative 4 are recovered. NMR analyses confirm the structure of the product. The average number of sulfur atoms (x) is 3.9±0.1.

Example 2

The reaction scheme with which this example is concerned is as follows:

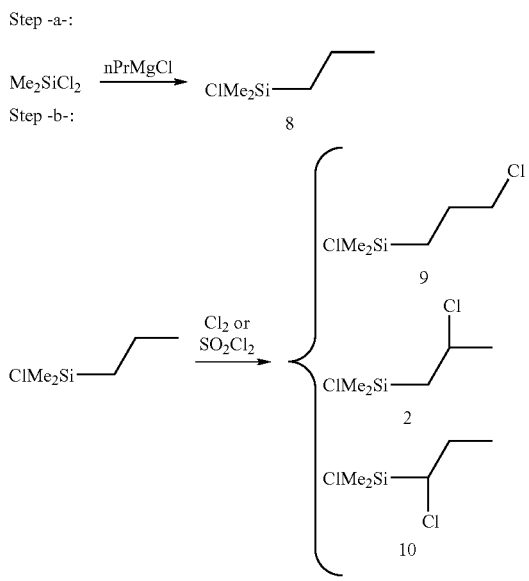

Step a): Synthesis of 1:

300 ml of dry THF and 129 g (1 mol) of Me$_2$SiCl$_2$ are introduced into a 1 l reactor under nitrogen. The mixture is cooled to 0° C. and [lacuna] mole of allylchloro Grignard in solution in THF is added dropwise. The mixture is allowed to return to 25° C. and left to react for 16 h. The solvent and the light compounds are then evaporated off. The rational mass is taken up with dry hexane. Filtration is performed. The cake is washed with dry hexane. 1 is recovered by distillation, with an isolated yield of the order of 80%. Structural analyses confirm the structure of 1. Bp: 110-112° C./755 mm Hg (Lit: 110° C./753 mm Hg).

Procedure idem for ClMe$_2$Si—CH$_2$—CMe=CH$_2$:

150-152° C./755 mm Hg (Lit. 133-134/741 mm Hg).

Step b) For Hydrochlorination: General Procedure 0.5 mol of allyl or methallyl silane and 0.006 mol of FeCl$_3$ and 200 ml of toluene are introduced into a 1 liter reactor under nitrogen. HCl gas is added with a flow rate of 4 liters/h, with vigorous stirring. The temperature increases to around 50-70° C. The amount of HCl introduced corresponds to the stoichiometry with respect to the unsaturation. The mixture is allowed to cool and the solvent is evaporated off. The chlorinated silanes are recovered by distillation under vacuum.

Step -c-:

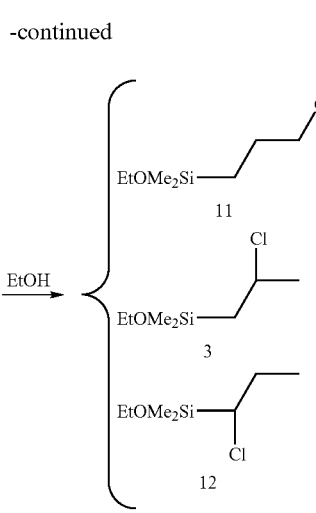

Use of the Intermediates 11, 3 and 12 in a Sulfidation Synthesis Reaction

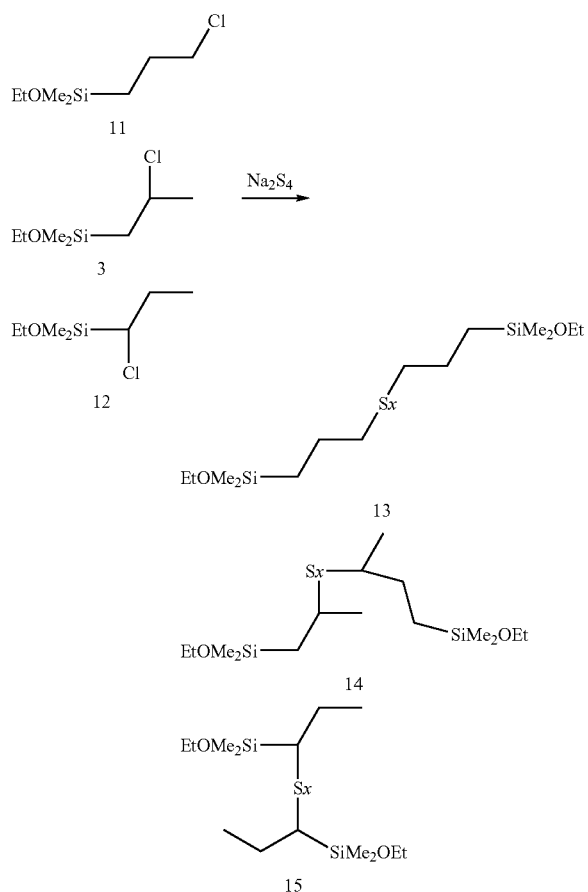

Step a): Synthesis of 8:

60 g (2.5 mol) of Mg chips and 100 ml of anhydrous THF are introduced into a 500 ml reactor, dry and under argon. 61 g (0.5 mol) of 1-bromopropane in 100 ml of anhydrous THF are then added dropwise. The reaction is exothermic (→reflux). This solution is then cooled to 25° C.

193.5 g (1.5 mol) of $Me_2SiCl_2$ are then introduced into a second 500 ml reactor, dry and under argon, and the first solution is run in slowly. The mixture is left at reflux for 24 h. The mixture is left to cool and is filtered under argon. Rapid distillation is carried out under vacuum and a rectification under vacuum then makes it possible to recover 55 g of n-PrSiMe$_2$Cl with an isolated yield of 80%.

NMR analyses confirm the chemical structure of this derivative. Bp/112-1130° C./730 mm Hg (Lit/100-110° C./720 mm Hg-L. BOKSANYI et al., Helv. Chim. Acta. (74) (1976) 717)).

Step b) For Hydrochlorination: General Procedure

The chlorination process is described in the literature. For example: L. SOMMER et al., J. Am. Chem. Soc., 68 (1946) 488 and V. MIRONOV et al., Izv. Akakd. Nauk. SSSR., Otdel. Khim. Nauk. (1955) 182.

A mixture of the three compounds is in general obtained, in a ratio which depends on the nature of the chlorinating agent. For $SO_2Cl_2$, the following ratios are observed: ~5/~45/~50 between 10/2/9.

The use of chlorine makes it possible to very greatly reduce the amount of derivative 10. The isolated yields are of the order of 75-80%.

Chlorination of n-PrSiMe$_2$Cl 136.5 g (1 mol) of n-PrSiMe$_2$Cl in 200 ml of $CCl_4$ are introduced into a 500 ml reactor under nitrogen. The mixture is brought to reflux and a solution of sulfuryl chloride (180 g, 1.33 mol) in 100 ml of $CCl_4$ and 2 g of benzoyl peroxide is added dropwise. The mixture is left to react for 2 h. The solvent is evaporated. A rectification under vacuum makes it possible to recover 110 g of the mixture of the subsequent three derivatives with a molar ratio of May 45, 1950 for the α, β, and γ chlorination positions.

Step c) Ethoxylation:

513 g (3 mol) of the mixture of silanes of 9, 2, and 10, and 300 ml of dry toluene are introduced into a 2 l reactor under nitrogen. 200 g of dry ethanol are added slowly. The temperature is kept at around 50° C. During this operation, the HCl is stripped with nitrogen. $NaHCO_3$ is subsequently added in order to neutralize the remaining last traces of HCl. Filtration is carried out and the solvent is then evaporated off. 273 g of the mixture of derivatives 11, 3 and 12 are recovered with a virtually quantitative yield.

Use of the Halogenated Alkoxysilanes 11, 3 and 12 as Synthesis Intermediates in Sulfidation Reactions:

91.9 g of sodium ethanolate (1.352 mol, i.e. the equivalent of 2 mol per mole of $H_2S$) in solution at 21 mass % in ethanol (438 g) and 250 ml of toluene are introduced, under a stream of argon, at the foot of a jacketed 1 liter reactor which is equipped with a refrigerant, a mechanical stirring device (Rushton turbine), a thermocouple, a gas (argon or $H_2S$) inlet pipe and an inlet for the peristaltic pump.

The mixture is stirred (200-300 rpm). A mass of 65 g of sulfur (2.031 mol, i.e. the equivalent of 3 mol per mole of $H_2S$) is then added.

After purging of the circuits with argon, the $H_2S$ (23 g, i.e. 0.676 mol) is introduced by bubbling by means of an immersed tube, i.e. for 45-60 min. Heating at 60° C. is carried out for 1 h so as to complete the conversion to anhydrous $Na_2S_4$.

The mixture is allowed to cool to 25° C. A mass of 244 g (1.352 mol) of the mixture of derivatives 11, 3 and 12 is added by means of a peristaltic pump in 30 min (flow rate: 10 ml/min).

The reaction mass is heated at 75° C. for 4 h. It is then allowed to cool. Filtration is carried out. The cake is washed twice with dry toluene. Evaporation is carried out under a vacuum pump (3-4×10² Pa) at 70° C. 279 g of the mixture of derivatives 13, 14 and 15 are recovered. NMR analyses confirm the structure of the product. The average number of sulfur atoms (x) is 3.8±0.1.

The invention claimed is:

1. A compound of the formula below

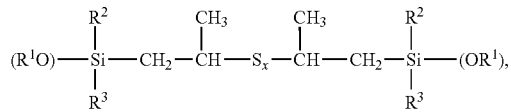

where:
- the symbol $R^1$ represents hydrogen, or a monovalent hydrocarbon chosen from a linear or branched alkyl radical having from 1 to 4 carbon atoms and a linear or branched alkoxyalkyl radical having from 2 to 8 carbon atoms;
- the symbols $R^2$ and $R^3$, which are identical or different, each represent a linear or branched alkyl radical having from 1 to 6 carbon atoms, an aryl radical having from 6 to 18 carbon atoms; an arylalkyl radical or an alkylaryl radical, where in said arylalkyl radical or said alkylaryl radical the aryl portion of the radical comprises $C_6$-$C_{18}$ aryl and the alkyl portion comprises $C_1$-$C_6$ alkyl; and
- x=an integer or fraction ranging from 1.5 to 10.

2. The compound of claim 1, where x is an integer or fraction ranging from 2 to 5.

3. The compound of claim 1, where $R^1$ is selected from the group consisting of methyl, ethyl, n-propyl, isopropyl, n-butyl, $CH_3OCH_2$—, $CH_3OCH_2CH_2$—, and $CH_3OCH(CH_3)CH_2$—.

4. The compound of claim 1, where $R^1$ is selected from the group consisting of methyl, ethyl, n-propyl and isopropyl.

5. The compound of claim 1, where $R^2$ and $R^3$ are independently selected from the group consisting of methyl, ethyl, n-propyl, isopropyl, n-butyl, n-hexyl and phenyl.

6. The compound of claim 1, where $R^2$ and $R^3$ are each methyl.

7. The compound of claim 1, where $R^1$ is selected from the group consisting of methyl, ethyl, n-propyl and isopropyl, $R^2$ and $R^3$ are each methyl, and x is an integer or fraction ranging from 2 to 5.

8. A compound of the formula below

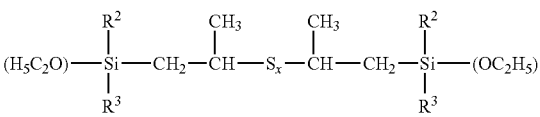

where x=an integer or fraction ranging from 3.8 to 4.0.

9. The compound of claim 8, where x is a fraction ranging from 3.7 to 3.9.

* * * * *

UNITED STATES PATENT AND TRADEMARK OFFICE
CERTIFICATE OF CORRECTION

PATENT NO. : 7,659,417 B2
APPLICATION NO. : 12/320567
DATED : February 9, 2010
INVENTOR(S) : Nathalie Guennouni et al.

Page 1 of 1

It is certified that error appears in the above-identified patent and that said Letters Patent is hereby corrected as shown below:

On the Title page item (73),

The Assignee is incorrectly listed as Rhodia Operations, Aubervilliers (FR) and should be listed as Rhodia Chimie, Aubervilliers (FR)

Col. 18, line 24,

Claim 8 contains a typographical error in the lower value of x. Claim 8 recites "x=an integer or fraction ranging from 3.8 to 4.0." The value 3.8 is a typographical error and should read 3.7. The specification provides support in the examples for a range of 3.7 to 4.0. In example 1, x is 3.9 ± 0.1 and in example 2, x is 3.8 ±0.1. Additional support is found in dependent Claim 9 which recites "The compound of claim 8, where x is a fraction ranging from 3.7 to 3.9." Dependent claim 9 must limit the range of claim 8, but does not due to typographical error. Therefore the lower value of 3.8 in claim 8 is a typographical error and needs to be changed to 3.7 to reflect the value in the specification.

Signed and Sealed this

Sixteenth Day of November, 2010

David J. Kappos
*Director of the United States Patent and Trademark Office*